(12) United States Patent
Hauptmann et al.

(10) Patent No.: US 12,059,483 B2
(45) Date of Patent: Aug. 13, 2024

(54) KIT OF PARTS AND PROCESS FOR FAST FIRING A POROUS ZIRCONIA ARTICLE IN COMBINATION WITH A SURFACE TREATING AGENT CONTAINING A GLASS POWDER

(71) Applicant: Solventum Intellectual Properties Company, Maplewood, MN (US)

(72) Inventors: Holger Hauptmann, Sindelsdorf (DE); Martin Goetzinger, Pflugdorf (DE); Jacqueline C. Rolf, River Falls, WI (US); Sybille Schmittner, Inning (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 896 days.

(21) Appl. No.: 16/975,188

(22) PCT Filed: Feb. 21, 2019

(86) PCT No.: PCT/IB2019/051396
§ 371 (c)(1),
(2) Date: Aug. 24, 2020

(87) PCT Pub. No.: WO2019/166920
PCT Pub. Date: Sep. 6, 2019

(65) Prior Publication Data
US 2020/0405586 A1    Dec. 31, 2020

(30) Foreign Application Priority Data

Feb. 28, 2018  (EP) .................................... 18159089
Sep. 4, 2018  (EP) .................................... 18192481

(51) Int. Cl.
*A61K 6/818*  (2020.01)
*A61K 6/833*  (2020.01)
(Continued)

(52) U.S. Cl.
CPC .............. *A61K 6/818* (2020.01); *A61K 6/833* (2020.01); *C03C 3/06* (2013.01); *C03C 3/076* (2013.01);
(Continued)

(58) Field of Classification Search
None
See application file for complete search history.

(56) References Cited

U.S. PATENT DOCUMENTS 7,985,119 B2   7/2011  Basler
8,141,217 B2   3/2012  Gubler
(Continued)

FOREIGN PATENT DOCUMENTS

CN   1931760    3/2007
CN   102499900   6/2012
(Continued)

OTHER PUBLICATIONS

EP 1972320 A1, English Translation from FIT (Year: 2008).*
(Continued)

*Primary Examiner* — Colin W. Slifka
(74) *Attorney, Agent, or Firm* — Ashley M. Dreis

(57) ABSTRACT

The invention relates to a process of producing a dental zirconia restoration, the dental zirconia restoration having an outer and an inner surface, the process comprising the step of firing a porous dental zirconia restoration and a glass until the porous dental zirconia restoration is sintered, the glass being located during the firing step on at least a portion of the outer surface of the porous dental zirconia restoration, wherein the zirconia material of the porous dental zirconia restoration and the glass are selected such that during the firing step the glass infiltrates the pores of the porous dental zirconia restoration to an extent of not more than 5 μm in depth. The invention also relates to a sintered dental zirconia
(Continued)

restoration obtainable by such a process and a kit of parts comprising a porous dental zirconia mill blank and a surface treating agent containing a glass for use in such a process.

18 Claims, 2 Drawing Sheets

(51) Int. Cl.
*C03C 3/06* (2006.01)
*C03C 3/076* (2006.01)
*C03C 4/00* (2006.01)
*C04B 41/00* (2006.01)
*C04B 41/50* (2006.01)
*C04B 41/86* (2006.01)
*C04B 111/00* (2006.01)
*C04B 111/80* (2006.01)

(52) U.S. Cl.
CPC ........ *C03C 4/0021* (2013.01); *C04B 41/0072* (2013.01); *C04B 41/009* (2013.01); *C04B 41/5022* (2013.01); *C04B 41/86* (2013.01); *C04B 2111/00836* (2013.01); *C04B 2111/805* (2013.01)

(56) References Cited

U.S. PATENT DOCUMENTS

| | | |
|---|---|---|
| 2008/0241551 A1 | 10/2008 | Zhang |
| 2012/0064490 A1 | 3/2012 | Rothbrust |
| 2012/0094823 A1* | 4/2012 | Watanabe ............. C04B 35/486 423/608 |
| 2017/0143456 A1 | 5/2017 | Carden |
| 2021/0002181 A1 | 1/2021 | Rothbrust |

FOREIGN PATENT DOCUMENTS

| | | | | |
|---|---|---|---|---|
| CN | 104744035 | | 7/2015 | |
| CN | 104774007 | | 7/2015 | |
| CN | 105439627 | | 3/2016 | |
| CN | 106904962 A | * | 6/2017 | ............. A61K 6/818 |
| DE | 20316004 | | 3/2004 | |
| EP | 1747765 | | 1/2007 | |
| EP | 1972320 A1 | * | 9/2008 | ............. A61K 6/0215 |
| JP | 2008-099953 A | | 5/2008 | |
| WO | WO 2001-013862 | | 3/2001 | |
| WO | WO 2002-045614 | | 6/2002 | |
| WO | WO 2008/060451 A2 | | 5/2008 | |
| WO | WO 2016-142234 | | 9/2016 | |
| WO | WO 2017-144644 | | 8/2017 | |
| WO | WO 2018-029244 | | 2/2018 | |
| WO | WO 2018/172544 | | 9/2018 | |

OTHER PUBLICATIONS

Ke et al, CN 106904962 A, English Translation from FIT (Year: 2017).*
"The Chroma Study of Alumina-zirconia Nano-composite Infiltrated Ceramic", Wang Tingting, pp. 6-7 and 10-29, *Chinese Outstanding Master's Theses Full-text Database: Medical and Health Science and Technology Series*, Apr. 15, 2008.
Spiridigliozzi, "Doped-Ceria Electrolytes-Synthensis, Sintering and Characterization", Applied Sciences and Technology, 2018, pp. 64-66.
ZirCAD Scientific Documentation IPS e.max, Jul. 2017, pp. 14.
International Search Report for PCT International Application No. PCT/IB2019/051396, mailed on May 9, 2019, 5 pages.
Drioli et al., "Comprehensive Membrane Science and Engineering", Second Edition, vol. 1, 2017, pp. 462-465.

* cited by examiner

KIT OF PARTS AND PROCESS FOR FAST FIRING A POROUS ZIRCONIA ARTICLE IN COMBINATION WITH A SURFACE TREATING AGENT CONTAINING A GLASS POWDER

FIELD OF THE INVENTION

The invention relates to a process of fast firing a porous zirconia dental material to final density in combination with a glass as part of a surface treating agent to obtain a glazed zirconia dental restoration. The invention also relates to a kit of parts comprising a porous dental material and a glass useful for producing such a dental restoration in a fast firing process.

BACKGROUND

Currently, dental restorations are typically produced by using one of the following approaches:

One approach is to use an open-pored oxide ceramic, which can be machined in-office or chair-side.

However, after the milling step a time-consuming heat treatment step is needed for obtaining a high strength material. During the heat-treatment step e.g. a glass material is infiltrated into a porous ceramic article to improve the strength of the article.

Such a process is described e.g. in US 2012/0064490 A1 (Rothbrust et al.). The infiltration of the infiltration substance into the pores of the open-pore oxide ceramic is typically done in vacuum and up to a depth of 2 to 90% of the thickness of the open-pore oxide ceramic. An infiltration depth in the range of 0.2 to 0.8 mm is reported.

Similarly, CN 104774007 B (Jinan University) describes a partially permeable, functionally graded zirconia ceramic material, which is infiltrated by a dental glass to obtain a three-layer structure of (1) a glass layer having a thickness of 0.2 mm, (2) a glass-permeated zirconia functionally graded layer having a thickness of 0.3 mm, and (3) a compact zirconia layer having a thickness of 0.5 mm. The glass used for the impregnation process has the composition: $La_2O_3$ 15%, $ZrO_2$ 5%, $Y_2O_3$: 5%, $SiO_2$: 20%, $B_2O_3$: 15%, BaO 15%, $Al_2O_3$: 15%, $TiO_2$: 4%, CaO: 4%, $CeO_2$: 1%, $Fe_2O_3$: 1%. Another approach is to grind fully sintered zirconia.

The strength level of fully sintered zirconia is higher compared to the strength of a glass ceramic material. However, the esthetic is sometimes not considered fully satisfying and the grinding itself is time-consuming as well. Further, a glazing or polishing step is typically needed for obtaining the desired esthetic gloss.

Such an approach is described e.g. in US 2017/143456 A1 (Carden et al.), where a fully sintered zirconia material is milled into a dental restoration with a chair-side milling machine. Another approach is to use a pre-sintered zirconia material.

The zirconia dental restoration is made in a dental laboratory by machining a pre-sintered (porous) block to a desired shape, thereby considering the shrinkage of the zirconia material during a later firing process. The firing process to full density typically takes at least 45 minutes.

After the firing step, a second so-called glaze-firing step is typically needed, particularly, if a glossy and highly esthetic dental restoration is desired.

The glazing of zirconia restorations is often recommended to reduce the risk of abrasion of the opposing tooth and because of esthetic reasons.

This is typically done by a lab technician in a dental lab. The lab technician manually applies layers of a glass powder on the surface of the sintered zirconia material and fire both at a much lower temperature compared to the sintering temperature used for sintering the porous zirconia material. The glass powder has typically a melting temperature of less than 900° C.

In the literature processes are described where a type of co-firing of a pre-sintered zirconia material with a glass-ceramic composition, particularly to improve the strength of the zirconia material and to avoid fracture problems.

WO 2016/142234 A1 (Gebr. Brasseler) describes a substance mixture for finishing dental restorations of zirconium dioxide, comprising a so-called over-burnable lithium silicate system and/or feldspar system dispersed in an organic liquid. The heat-treatment is typically done at a temperature of 850 to 950° C. It is stated that the surface of the zirconium dioxide is preferably free of pores.

US 2008/0241551 A1 (Zhang et al.) suggests a method of preparing a functionally graded glass/zirconia/glass sandwich material comprising the steps of a) applying a certain powdered glass-ceramic composition to accessible surfaces of a pre-sintered zirconia substrate, b) infiltrating the glass-ceramic composition into the substrate; and c) densifying the substrate by heating.

In the example section, a heating and cooling rate of 800° C./h is reported. For the overall infiltration and densification process 2 hours are needed. The thickness of the gradient layers is said to be in a range of 60 to 150 μm.

If such a process is applied to porous dental zirconia materials, the resulting article does not meet the requirements of an esthetic dental restoration.

Further, if the glass-ceramic composition is only applied to certain areas of the surface of the dental restoration (e.g. the outer surface of a dental zirconia crown precursor), the sintered dental restoration may show distortion caused by different sintering and shrinkage behavior of the two materials used.

SUMMARY

There is a desire for a process enabling the practitioner to produce zirconia dental restorations chairside, i.e. a process, which does not require the use of a dental lab. Particularly, there is a desire for a fast procedure.

Ideally, the time needed from scanning the dental situation in the mouth of a patient to the seating of the dental restoration should be less than 50 min.

Ideally, the time needed for sintering and glazing a porous dental zirconia restoration should be reduced to less than 30 min. Further, ideally, the process should be easy to perform and yield predictable results.

One or more of the above objectives are addressed by the invention described in this document.

In one embodiment, the invention features a process of producing a dental zirconia restoration as described in the claims and the present text the dental zirconia restoration having an outer and an inner surface, the process comprising the step of
  firing a porous dental zirconia restoration and a glass until the porous dental zirconia restoration is sintered,
  the glass being located on at least a portion of the outer surface of the porous dental zirconia restoration during the firing step, wherein the zirconia material of the porous dental zirconia restoration and the glass are selected such that during the firing step the glass infiltrates the pores of the porous dental zirconia restoration to an extent of not more than 5 μm in depth.

The invention also relates to a sintered zirconia dental restoration obtainable or obtained by such a process.

The invention further relates to a kit of parts comprising a porous dental zirconia mill blank and a surface treating agent comprising a glass as described in the claims and the present text, and the use of such a kit for producing a sintered zirconia dental restoration in a single firing process.

A further aspect of the invention is directed to the use of the kit of parts or its respective parts individually as described in the claims and the present text for producing dental zirconia restorations.

Unless defined differently, the following terms should have the given meanings:

The term "dental article" means any article which is to be used in the dental field, especially for producing a dental restoration and parts thereof.

A dental article typically has a 3-dimensional inner and outer surface including convex and concave structures. Compared to other articles such as pottery or paving stones, a dental article is small and filigree. The thickness of the dental article can vary from very thin, e.g. at the edges and rims (below 0.1 mm) to considerably thick, e.g. in the biting area (up to 8 mm). Sections bridging the crown portions in dental bridges might have a thickness up to 20 mm.

The outer surface typically has an overall convex shape, whereas the inner surface typically has an overall concave shape.

Typically, the dental article described in the present text comprises or essentially consists after sintering of a polycrystalline ceramic material comprising yttrium stabilized $ZrO_2$.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons), monolithic dental restorations (i.e. restorations which do not need to be veneered) and parts thereof. The surface of a tooth is not regarded a dental article.

A dental article should not contain components which are detrimental to the patient's health and thus free of hazardous and toxic components being able to migrate out of the dental article.

By "dental mill blank" is meant a solid block (3-dim article) of material from which a dental article, dental workpiece, dental support structure or dental restoration can and typically is to be machined in any subtractive process, e.g. aside from milling also by grinding, drilling etc.

A dental mill blank has a geometrically defined shape and comprises at least one flat surface. A so-called "free form surface" is not regarded as "geometrically defined". In this respect, the shape of a dental restoration (e.g. crown or bridge) itself is not regarded a dental mill blank.

"Zirconia article" shall mean a 3-dimensional article wherein at least one of the x,y,z dimensions is at least 5 mm, the article being composed of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures for zirconia ceramics include tetragonal, monoclinic, cubic and mixtures thereof.

"Monolithic dental restoration" means a dental ceramic article onto the surface of which no facing or veneer has been attached. That is, the monolithic dental restoration is essentially composed of only one material composition. However, if desired, a thin glazing layer can be applied.

"Glass" means an inorganic non-metallic amorphous material which is thermodynamically an under-cooled liquid. Glass refers to a hard, brittle, transparent solid. Typical examples include soda-lime glass and borosilicate glass. A glass is an inorganic product of fusion which has been cooled to a rigid condition without crystallizing. Most glasses contain silica as their main glass forming component and a certain amount of intermediate and modifier oxides. The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then crystallize by a nucleation and crystallization heat treatment. Glass ceramics may refer to a mixture of lithium-, silicon-, and aluminium-oxides.

The porous dental material described in the present text does not contain a glass-ceramic.

A "powder" means dry bulk composed of a large number of fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

A "porous material" refers to a material comprising a partial volume that is formed by voids or pores in the technical field of ceramics.

Accordingly, an "open-celled" structure of a material sometimes is referred to as "open-porous" structure, and a "closed-celled" material structure sometimes is referred to as a "closed-pored" structure. A material having an open-celled or open-porous structure can be passed through by e.g. gases.

Typical values for an "open-celled material" are between 15% and 75% or between 18% and 75%, or between 30% and 70%, or between 34% and 67%, or between 40% and 68%, or between 42% and 67%.

The term "closed-celled" relates to a "closed porosity". Closed cells are those cells which are not accessible from the outside and cannot be infiltrated by gases or liquids under ambient conditions.

The "average connected pore diameter" means the average size of the open-celled pores of a material. The average connected pore diameter can be calculated as described in the examples section.

The term "calcining" refers to a process of heating a solid material to drive off at least 90 percent by weight of volatile chemically bond components (e.g., organic components) (vs., for example, drying, in which physically bound water is driven off by heating). Calcining is done at a temperature below a temperature needed to conduct a pre-sintering step.

The terms "sintering" or "firing" are used interchangeably. A porous ceramic article shrinks during a sintering step, that is, if an adequate temperature is applied. The sintering temperature to be applied depends on the ceramic material chosen. For $ZrO_2$ based ceramics a typical sintering temperature range is 1,100° C. to 1,550° C. If the sintering is done with high heating-rates, higher temperatures may be required. Sintering typically includes the densification of a porous material to a less porous material (or a material having less cells) having a higher density, in some cases sintering may also include changes of the material phase composition (for example, a partial conversion of an amorphous phase toward a crystalline phase).

A dental zirconia article is classified as "pre-sintered", if the dental zirconia article has been treated with heat (temperature range of 900 to 1,100° C.) for 1 to 3 h to such an extent that the raw breaking resistance of the dental ceramic measured according to the "punch on three ball test" ISO 6872:2015 is within a range of 15 to 55 MPa or 20 to 50 MPa.

A pre-sintered dental ceramic usually has a porous structure and its density (usually about 3.0 $g/cm^3$ for an yttrium stabilized $ZrO_2$ ceramic) is less compared to a completely sintered dental ceramic framework (usually about 6.1 $g/cm^3$ for an yttrium stabilized $ZrO_2$ ceramic).

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than +/−5% or +/−2% or +/−1%.

"Colouring ions" shall mean ions which have an absorption in the spectral range visible to the human eye (e.g. 380 to 780 nm), which results in a coloured solution (visible to the human eye), if the colouring ions are dissolved in water (e.g. about 0.6 mol/l) and/or cause a colouring effect in the zirconia article which has been treated with a colouring solution and sintered afterwards. Coloring ions may also be present in the powder before the powder used for producing the zirconia article is compacted.

A "fluorescing agent" shall mean an agent showing fluorescence in the region of visible light (380 to 780 nm).

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

The terms "comprise" or "contain" and variations thereof do not have a limiting meaning where these terms appear in the description and claims. The term "comprise" shall include also the terms "consist essentially of" and "consists of".

Adding an "(s)" to a term means that the term should include the singular and plural form. E.g. the term "additive (s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

"And/or" means one or both. E.g., the expression component A and/or component B refers to a component A alone, component B alone, or to both component A and component B.

DETAILED DESCRIPTION

Figure 1:
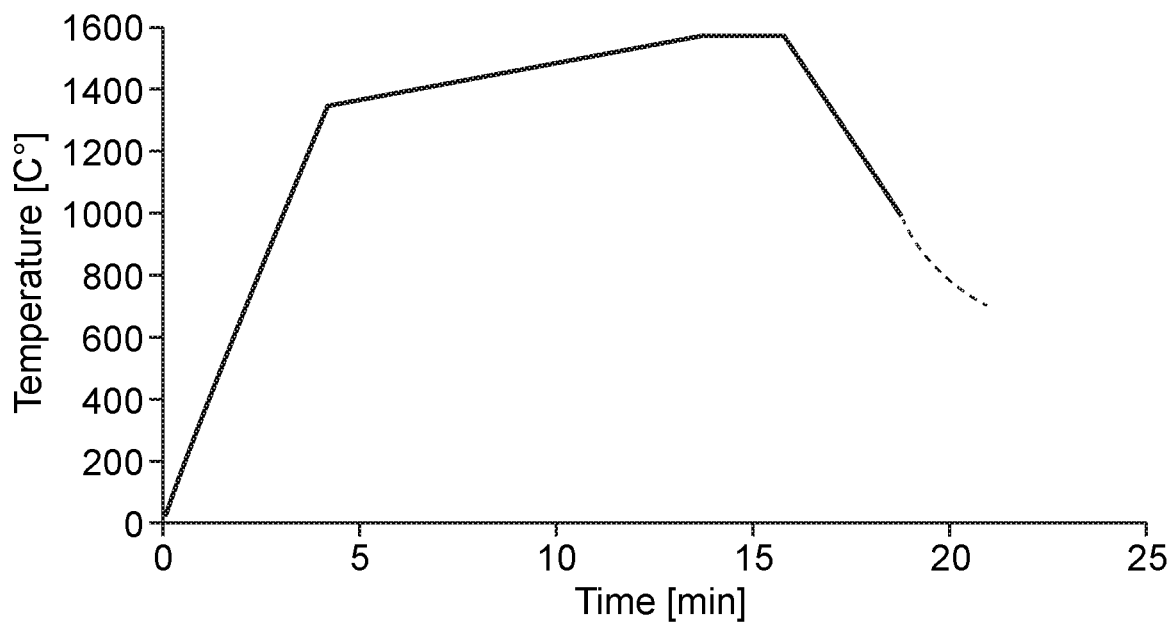
FIG. 1 shows an example of a sinter protocol useful for sintering yttrium stabilized zirconia.

The general idea of the invention is based on the finding, that an esthetic dental zirconia restoration can be obtained by fast firing a porous zirconia article together with glass on its surface.

By adjusting the properties of the porous zirconia precursor and the glass particles, the glass does only impregnate a small region of the porous zirconia interface.

It was found that a deeper impregnation of the glass typically has a negative impact on the esthetics as the overall translucency of the article will be reduced.

Further, the risk of a possible distortion of the article during the sintering process is reduced, if the impregnation depth is reduced.

In particular, if the melting behavior of the glass is adjusted to the shrinkage behavior of the porous zirconia article during the sintering process, a reduced penetration depth of the glass into the open-pores of the porous zirconia material can be achieved. The invention described in the present text provides the following advantages. It saves time for the practitioner. It also simplifies the sintering process.

The process described in the present text allows a fast sintering by applying heating rates of at least 3 K/sec or at least 4 K/sec or at least 5 K/sec.

The firing process described in the present text combines the steps of sintering the dental zirconia material and the glazing of that material in one step. There is no need for a separate glazing or veneering step which is typically performed in a dental lab. The firing step can be completed within less than 30 or less than 25 min.

The obtained zirconia article meets the requirements for an esthetic dental zirconia restoration.

The intermediate layer section is thin enough so that the zirconia article shows sufficient translucency (i.e. reduced opacity).

In addition, the obtained sintered dental zirconia article has adequate strength and does not show cracks. The invention relates to a process of producing a dental zirconia restoration.

The process comprises the step of firing a porous zirconia dental restoration and a glass to obtain a sintered dental zirconia restoration.

During the firing step, the glass is located on at least a portion of the surface of the porous dental zirconia restoration.

The glass and the zirconia material of the porous zirconia restoration are selected such that during the firing step, the glass does not infiltrate the pores of the porous zirconia material to an extent of more than 5 μm or more than 4 μm or more than 3 μm or more than 2 μm or more than 1 μm in depth.

This is in contrast to impregnation procedures suggested in the prior art (e.g. CN 104774007 B), where the impregnation depth is in a range of 0.3 mm (300 μm) or more.

The selection of the porous dental zirconia restoration and the glass suggested in the present text is usually based on material and physical properties of the porous zirconia restoration and the glass. Typical physical properties include viscosity of the glass during the firing step, surface tension of the glass, pore size and sintering behaviour of the porous zirconia material before the firing process is started, and combinations thereof.

A glass having a viscosity of at least 0.08 MPa*s ($10^{4.9}$ Pa*s) or at least 0.1 MPa*s ($10^5$ Pa*s) or at least 0.2 MP*s ($10^{5.3}$ Pa*s) or at least 0.5 MP*s ($10^{5.7}$ Pa*s) at the temperature where the pores of the porous dental zirconia restoration close was found to be particularly useful.

Useful viscosity ranges for the glass include $10^{4.9}$ Pa*s (0.08 MPa*s) to $10^{7.5}$ Pa*s (30 MPa*s) or $10^5$ Pa*s (0.1 MPa*s) to $10^{7.3}$ Pa*s (20 MPa*s) or $10^{5.3}$ Pa*s (0.2 MPa*s) to $10^{7.2}$ Pa*s (15 MPa*s).

If desired, the viscosity of the glass in Pa*s can also be expressed in logio scale. E.g. a viscosity of 1 MPa*s can also be expressed as logio (Pa*s) 6 or $10^6$ Pa*s.

For comparison, commercially available glasses which are used for glazing a sintered dental zirconia restoration typically have a viscosity $\log_{10}$ (Pa*s) at 1,300° C. in the range of 2 to 4 or 1.5 to 3.

If desired, the closing of the pores of a porous zirconia article during sintering can be determined by scanning electron microscopy (SEM).

Instead of determining the viscosity of a glass by experiment, it is also possible to calculate the viscosity based on its chemical composition as outlined in the example section. Reliable computer programs are commercially available and widely used (e.g. glass database from SciGlass).

According to one embodiment, the viscosity of the glass is at least $10^{4.9}$ Pa*s or at least $10^5$ Pa*s or at least $10^{5.3}$ Pa*s or at least $10^{5.7}$ Pa*s at a temperature of 1,300° C. for a porous zirconia material having an average connected pore diameter from 40 nm to 150 nm. E.g. a suitable viscosity range is $\log_{10}$ (Pa*s) 5 to $\log_{10}$ (Pa*s) 7.5.

According to another embodiment, the viscosity of the glass is at least $10^{4.9}$ Pa*s or at least $10^5$ Pa*s or at least $10^{5.3}$ Pa*s at a temperature of 1,300° C. for a porous zirconia material having an average connected pore diameter in the range from 40 nm to less than 90 nm. E.g. a suitable viscosity range is $\log_{10}$ (Pa*s) 5 to $\log_{10}$ (Pa*s) 7.5.

According to another embodiment, the viscosity of the glass is at least $10^6$ Pa*s or at least $10^{6.3}$ Pa*s or at least $10^{6.7}$ Pa*s at a temperature of 1,300° C. for a porous zirconia material having an average connected pore diameter in the range from 90 nm to 150 nm. E.g. a suitable viscosity range is $\log_{10}$ (Pa*s) 6 to $\log_{10}$ (Pa*s) 7.5.

The thickness of the infiltration zone is typically within a range of 10 nm to 5 μm or 20 nm to 3 μm or 30 nm to 2 μm.

If desired, the thickness of the infiltration zone can be determined as described in the example section, e.g. by SEM.

If the thickness of the infiltration zone is higher (e.g. above 5 μm), the translucency of the sintered dental zirconia article is often considered to be not acceptable for use as dental restoration.

The overall process of producing a dental zirconia restoration typically comprises a couple of different steps:

First, a porous dental zirconia restoration is machined from a porous zirconia dental mill blank.

The machining step can be done with a milling, drilling, cutting, carving, or grinding device. Those devices are commercially available e.g. from Roland (DMX™ mills), or Sirona (CEREC™ inLab CAD/CAM) and others.

Useful milling parameters include:
rotary speed of milling tool: 5,000 to 40,000 revolutions/min;
feed rate: 20 to 5,000 mm/min;
milling cutter diameter: 0.8 to 4 mm.

If desired, the machined porous dental zirconia restoration is cleaned, e.g. removing milling dust with pressurized air.

As the porous dental zirconia mill blank is used for producing the porous dental zirconia restoration, the material of the porous dental zirconia mill blank is the same as the material of the porous dental zirconia article. The porous dental zirconia mill blank has typically the shape of a block or disc.

If the porous dental zirconia mill blank has the shape of a block, the porous zirconia dental mill blank has typically the following dimensions:
x-dimension: 12 to 45 mm, or 15 to 40 mm,
y-dimension: 12 to 70 mm, or 15 to 60 mm,
z-dimension: 10 to 40 mm, or 15 to 25 mm.

If the porous dental zirconia mill blank has the shape of a disc, the porous dental zirconia mill blank has typically the following dimensions:
x, y-dimension: 90 to 110 mm, or 95 to 105 mm,
z-dimension: 5 to 35 mm, or 10 to 30 mm.

Attaching or fixing the dental zirconia mill blank to a machining device, especially to the clamping appliance(s) of such a device, can also be accomplished by providing the blank with suitable means therefore. Suitable means include frame(s), notch(es), stub(s), mandrels and combinations thereof.

In another embodiment, the dental zirconia mill blank is fixed to or contained in a holding device. The holding device containing the dental mill blank may then function as a means for attaching the blank to a machining device.

Fixing of the dental zirconia mill blank to a holding device can be affected by clamping, gluing, screwing and combinations thereof.

Useful holding devices include frames (open and closed), stubs or mandrels. Using a holding device may facilitate the production of the dental article with a machining device.

Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The porous zirconia mill blank can be produced as follows:

The porous zirconia material of the dental mill blank can be obtained by a process comprising the steps of:

mixing the powders of the respective oxides contained in the material to obtain a powder mixture and pressing the powder mixture.

Mixing of the oxide powders can be achieved by shaking the powders or putting the powders in a mill (e.g. ball mill) and milling the powders until a homogenous powder mixture is obtained. Further possible mixing equipment can include sieves or granulators.

To facilitate the pressing step(s), pressing aids can be added, if desired.

Suitable pressing aids include binders, lubricating additives and mixtures thereof.

If desired, these aids can be added to the zirconia oxide powder being the main component of the powder mixture.

Suitable metal oxide powders are commercially available from various sources including Tosoh Company (Japan).

The powder mixture is then placed in a mould and pressed into the shape of a dental mill blank.

The applied pressure is typically in the range of 150 to 300 MPa. Alternatively, the applied pressure is set so that the pressed ceramic body reaches a certain density, e.g. in the case of zirconia ceramic a density of 2.8 $g/cm^3$ to 3.5 $g/cm^3$.

The article obtained after pressing the powder mixture can be machined or sliced into any desired shape. If desired, a calcining step can be done.

In a further step, a heat treatment is applied to the compacted composition to obtain a porous dental mill blank.

The temperature of the heat treatment is typically in a range of 800 to 1100° C. or 900 to 1,000° C. The heat treatment is typically applied for a duration of 30 to 70 hours or 35 to 60 hours.

The porous zirconia dental mill blank is typically provided to the customer in a form allowing the mounting of the dental mill blank in a milling machine.

Either the top or bottom surface of the porous zirconia dental mill blank typically contains a marking element (e.g. printing or carving) which facilitates the correct orientation of the dental mill blank in a milling machine.

According to the invention, a surface treating agent comprising a glass is applied to at least a part of the surface of the porous dental zirconia restoration to be sintered. The porous dental zirconia is in dry state.

The surface treating agent is applied to the outer surface of the porous dental zirconia restoration.

The surface treating agent is typically applied at least to those parts of the outer surface of the porous dental zirconia restoration, which remain visible in the mouth of a patient after the sintered dental zirconia restoration has been fixed to the tooth structure of the patient.

Typically, the surface treating agent is applied to at least 30% or at least 50% or at least 70% of or at least 90% of the outer surface of the porous dental zirconia restoration.

The surface treating agent is typically not applied to the inner surface of the porous dental zirconia restoration.

A surface treatment of the inner surface may be detrimental for a later fixation process (e.g. cementing step) of the sintered dental zirconia restoration on a tooth surface.

Thus, the inner surface of the porous dental restoration is not treated with the surface treating agent to an extend which would negatively affect such a fixation process.

The application of the surface treating agent is typically done with a suitable application instrument. Suitable application instruments are described further down below.

E.g., the application of the surface treating agent can be done by brushing or by spraying.

This is particularly feasible, if the surface treatment agent is provided as dispersion of a glass powder in a liquid.

However, the glass can also be applied in a different form, e.g. in the form of a coping, facing, paste or sheet.

If the surface treating agent comprises a liquid or dispersant for the glass, the liquid or dispersant may be evaporated before a firing step is conducted. Thus, before the sintering process is started, optionally a drying step is conducted.

In a next step, a firing step of the porous dental zirconia restoration with the surface treating agent comprising a glass on its outer surface is conducted.

During the firing process, the porous dental article is sintered to its final shape, thereby undergoing changes with regard to dimension, density, hardness, bending strength and/or grain size.

The firing step should be accomplished under conditions which results in a dental ceramic restoration having an acceptable tooth like colour (e.g. a colour which fits into the Vita™ shade guide.

Generally, the firing conditions are adjusted such that the sintered dental ceramic restoration has a density of equal or greater than 98% or 99% compared with the theoretically achievable density. The process described in the present text comprises a first heat-treatment segment.

The first heat-treating segment is done with a heating rate of at least 3 K/sec or at least 4 K/sec or at least 5 K/sec.

The heating rate should not exceed a rate of 15 K/sec or 12 K/sec or 10 K/sec as this may negatively affect the translucency of the final product.

Typical heating rates are thus within a range of 3 to 15 K/sec or 4 to 12 K/sec.

With such heating rates a temperature increase of at least 180 to 240° C./min can be obtained.

Thus, the temperature at which the sintering of the dental porous zirconia article starts can be reached within a time frame of 4 to 8 min.

In contrast to this, sintering processes described in the prior art typically require at least 45 min to reach this temperature.

The first heat-treating segment is typically conducted until a temperature level of 75 to 90% or 80 to 88% of the final sintering temperature for the dental zirconia article is reached.

For a zirconia material, the respective temperature is typically in the range of 1,200 to 1,400° C. or 1,250 to 1,350° C.

At this temperature, the sintering has partially started, but the dental zirconia article still contains pores, in particular open pores.

If the first heat-treatment segment is performed to a temperature level above the above-mentioned ranges of the final sintering temperature (in ° C.), the resulting dental zirconia article sometimes shows distortions or cracks.

The final sintering temperature is the temperature at which the pores (open and closed pores) of the porous zirconia material close under ambient pressure (about 1,013 hPa). If desired, this state can be determined by using a scanning electron microscope.

A finally sintered zirconia material typically has a density of at least 99% of the theoretical density.

The final sintering temperature typically corresponds to the temperature reached after the second heat-treatment segment.

For zirconia articles, the final sintering temperature is typically within a range of 1,500 to 1,650° C.

The first heat-treating segment is typically followed by a second heat-treating segment back-to-back.

The second heat-treating segment is typically conducted at a heating rate which is different from the heating rate of the fist heat-treating segment.

According to one embodiment, the heating rate of the second heat-treating segment is lower than the heating rate of the first heat-treating segment.

Heating rates which can be used are typically 2K/sec (or less) or 1K/sec (or less).

The second heat-treating segment is typically done until the sintering temperature of the dental zirconia article is reached.

The temperature at the end of the second-heat-treating segment typically corresponds to the final sintering temperature.

The sintering temperature is typically at least 1,500° C. or at least 1,520° C. or at least 1,550° C.

The sintering temperature is typically not more than 1,650° C. or not more than 1,600° C.

The duration of the second heat-treating segment is typically dependent on the size and dimensions of the porous dental zirconia article to be sintered.

The duration of the second heat-treating segment is typically in the range of 1 to 15 min or 2 to 14 min or 5 to 12 min.

Larger dental articles, in particular dental articles having a wall thickness above e.g. 15 mm typically require more time than smaller articles.

The second heat-treating segment is typically followed by a third heat-treating segment back-to-back.

During the third heat-treating segment, the temperature is typically not increased further, but maintained for a so-called dwell time.

A suitable dwell time is typically 8 min to 1 min or 5 min to 1 min or 3 min to 1 min.

During the third heat-treatment segment, the final sintering takes place and the remaining pores of the dental zirconia article close.

As indicated above, the duration of the second heat-treating segment is typically dependent on the size and dimensions of the dental zirconia article to be sintered. The third heat-treating segment is typically followed by a cool-down segment.

During the cool-down segment, the sintered dental zirconia article is cooled down to about 1,000° C. When this temperature is reached, the furnace is opened automatically to cool the sintered dental zirconia to room temperature (23° C.).

The cooling rates can be same as or different from the heating rates mentioned above. Typical cooling rates may be in the range of at least 3K/sec or at least 4K/sec or at least 5K/sec.

An example of a suitable sintering protocol is shown in FIG. 1.

In this example, the sintering protocol contains the following segments:

a) a first heat-treating segment up to a temperature of about 1,350° C., which is reached within about 4 min, b) a second heat-treating segment up to a temperature of about 1,580° C., which is reached within about 2 min, c) a third heat-treating segment (dwell time) for about 2 min and d) a cool-down segment to a temperature of about 1,000° C., which is reached within about 3 min.

The heat-treating segments are typically conducted at ambient pressure and in air or sometimes in inert gas (e.g. nitrogen, argon).

The heat-treating segments and cooling-down segment described above can be compiled to a so-called sintering protocol.

FIG. 1 shows an idealized example of a suitable sintering protocol. As known to the skilled person, due to delays in the control engineering, there might be small temperature deviations (e.g. +/−3%), in particular at the interface between the respective segments.

According to one embodiment, the firing step used for producing a sintered dental zirconia restoration is characterized by the following features alone or in combination:

First segment of heat-treating: heating rate of 3 to 7 K/sec; duration: 8 min or less;

Second segment of heat-treating: heating rate of 0.2 to 1.0 K/sec or 0.3 to 0.6 K/sec; duration: 25 min or less;

Third segment of heat-treating: heating rate of about 0 K/sec; duration: 8 min or less or 5 min or less or 3 min or less;

Cooling-down segment: cooling rate 3 K/sec or more; duration: 6 min or less.

The overall time needed for heat-treating (comprising the first, second and third heat-treating segments) and cool-down the dental zirconia article is typically 30 min or less, 25 min or less.

The overall time typically also depends to some extent on the volume of the zirconia article to be sintered. Large articles typically require a longer heat-treating time than smaller articles.

Characterizing the volume of the article to be sintered by fitting the article into an artificial sphere can help to select the appropriate sintering protocol. Such an approach is described in WO 2018/029244 A1 (Sirona).

An oven which can be used for the process described in the present text is commercially available from Dentsply Sirona (SpeedFire™).

A suitable furnace is also described in WO 2017/144644 A1 (Sirona). This furnace is for carrying out a heat treatment of a dental replacement part and comprises an induction coil, a radiant heater, an insulation layer and a furnace chamber. Further, the furnace has a cooling system to control the internal temperature of the furnace chamber.

Generally, useful heat-treating conditions which are applied during the firing step can be characterized by the following features alone or in combination:

a) heating rate: 3 to 7 K/sec or 5 to 7 K/sec;

b) sintering temperature: at least 1,400° C. or at least 1,450° C. or at least 1,500° C.;

c) atmosphere: air or inert gas (e.g. nitrogen, argon);

d) duration: until a density of at least 95 or at least 98 or at least 99% of the final density of the material has been reached;

e) dwell time: 0 to 10 min or 1 to 5 min;

f) pressure: ambient pressure.

A combination of the following features is sometimes preferred: a) and b); a), b) and d); a), b), c), d) and e).

The firing temperature and dwell time (that is the time during which the article is kept at that temperature) are often correlated.

A higher temperature typically requires only a short dwell time. Thus, the dwell time, may last from 0 (e.g. if the firing temperature is 1,550° C.) to 10 min (e.g. if the firing temperature is 1,100° C.).

Alternatively, to the above described fast heat treatment process where high heating rates are used, the sintering process can also be conducted by using lower heating rates.

A respective sintering protocol can be characterized as follows:
sintering temperature: 1,350 to 1,600° C.;
duration: 50 to 360 min;
heating rate: 1 to 30° C./min.

The material of the porous dental zirconia article has an average connected pore diameter from 40 to 150 nm and can further be characterized by the following parameters, alone or in combination:
a) BET surface: 5 to 15 m²/g or 5.5 to 11 m²/g;
b) density: 2.5 to 4 g/cm³ or 2.85 to 3.35 g/cm³;
c) average grain size: 50 to 200 nm or 60 to 180 nm or 80 to 160 nm.

The following combination of features is sometimes preferred: a) and b); a) and c); a), b) and c).

The material of the porous dental zirconia article may also be characterized as follows:
a) average connected pore diameter from 40 to 150 nm,
b) density: 2.85 to 3.35 g/cm³;
c) average grain size: 50 to 200 nm.

Using a material with an average connected pore diameter from 40 to 150 nm can be beneficial, because it is comparably easy to produce (e.g. by compacting a powder and conducting a pre-sintering step).

Further, the average connected pore-diameter is in a range which allows the limitation of the interpenetration of the glass during the sintering process to a depth of not more than 5 μm.

With increasing average connected pore diameter, the viscosity of the glass should preferably be adjusted, e.g. a glass with a higher melting behaviour should be used.

Using a porous dental zirconia article, wherein the material has a BET surface in the range specified above was found to be sometimes advantageous, because it ensures an adequate sintering activity of the material before and during the heat-treating process, in particular during the first heat-treating segment having a high heating rate.

An adequate sintering activity can be beneficial for obtaining a zirconia article showing the desired translucency within a short sintering time.

Without wishing to be bound to a certain theory, it is believed that, if the BET surface is too high, there are too many pores in the porous dental zirconia article to be sintered. This might negatively influence the sintering of the article and make it more difficult to achieve a dental zirconia article having adequate strength and/or translucency.

If on the other hand the BET surface is too low, it is believed that the porous zirconia article does not have an adequate sintering activity. This might negatively influence the sintering behaviour (e.g. sintering shrinkage, outgassing of remaining sintering aids) of the porous dental zirconia article during the first heat-treating step.

When referring to the BET surface, the surface of the porous article is meant, not of the powder used for producing the article.

Alternatively, or in addition to the BET surface, the density may also be used for characterizing the material of the porous dental zirconia restoration, because the density is often related to the overall pore volume.

Alternatively, or in addition, the material of the porous dental zirconia article can be characterized by the following parameters alone or in combination:
a) biaxial flexural strength: 15 to 55 determined according to ISO 6872:2015 applying the punch on 3 balls test adapted to measurement in porous state (measurement set up: 3.6 mm punch diameter, 0.1 mm/min load speed, 2 mm sample thickness, support ball diameter 6 mm, 14 mm diameter of supporting balls);
b) Vickers hardness: 15 to 150 (HV 0.5) or 20 to 140 (HV 0.5);
c) coefficient of thermal expansion: $8.5*10^{-6}$ $K^{-1}$ to $11.5*10^{-6}$ $K^{-1}$.

The following combination of features is sometimes preferred: a) and b); a) and c); a), b) and c).

If desired, the respective features can be determined as described in the example section.

If the Vickers hardness of the material is too low, the machinability could negatively affect the quality (edge chipping or breaking of the workpiece) as well as in the ease of manual reworking to individualize the frame of a dental restoration or a monolithic restoration.

If the Vickers hardness of the material is too high, the wear of the machining tools may increase and shorten tool life to an unacceptable level or the tool could break and destroy the workpiece.

It was found that, if the biaxial flexural strength of the material is too low, the material may tend to crack during the milling process or during the manual finishing by a dental technician.

On the other hand, if the biaxial flexural strength of the material is too high, the processing of the material by a milling machine is often not possible with reasonable efforts. The milling tool used or the milled material sometimes tend to chip or break. In such a case, the shaping of the material had to be done by grinding, e.g. using a Cerec™ grinding machine (Sirona).

In order to further reduce the risk of cracks, the coefficient of thermal expansion (CTE) of the zirconia material should be adjusted to the CTE of the glass used during the fast firing process.

The material of the porous dental zirconia article comprises ceramic components and stabilizing components.

Optionally, colouring components and fluorescing components can be present.

The ceramic components are typically selected from oxides of Zr, Hf, Al and mixtures thereof.

Thus, in addition to zirconia, the material of the porous zirconia dental mill blank typically comprises oxides of Hf and optionally Al, typically in only small amounts.

Stabilizing component(s) are typically selected from oxides of Y, Mg, Ca,Ce and mixtures thereof (e.g. $Y_2O_3$, MgO, CaO, $CeO_2$), wherein oxides of Y are often preferred.

If present, colouring component(s) are typically selected from oxides of Fe, Mn, Cr,Ni, Co, Er, Pr, Nd, V, Tb, in particular selected from the oxides of Mn, Er, Pr, Co, V, Tb and mixtures thereof (e.g. $MnO_2$, $Er_2O_3$, $Pr_2O_3$, CoO, $V_2O_5$, $Tb_2O_3$).

If present, the fluorescing agent is typically selected from oxides of Bi and mixtures thereof.

Ceramic components are typically present in an amount of 80 to 95 wt. % or 85 to 95 wt. % or 90 to 95 wt. % with respect to the weight of the porous dental mill blank.

Stabilizing components are typically present in an amount of 3 to 12 wt. % or 5 to 10 wt. % or 6 to 10 wt. % with respect to the weight of the porous dental mill blank.

If present, colouring components are typically present in an amount of 0.01 to 2 wt. % or 0.02 to 1.5 wt. % or 0.03 to 1.2 wt. % with respect to the weight of the porous dental mill blank.

If present, the fluorescing agent is typically present in an amount of 0 to 1 wt. % or 0.005 to 0.8 wt. % or 0.01 to 0.1 wt. % with respect to the weight of the porous dental mill blank.

The wt. % are calculated based on the amount of the respective oxides or the ceramic components, stabilizing components, colouring components and fluorescing agents.

For obtaining an aesthetic dental article, the following concentrations were found to be useful:
ceramic components: 80 to 95 wt. % or 85 to 95 wt. %,
stabilizing components: 3 to 12 wt. % or 5 to 11 wt. %,
colouring components: 0 to 2 wt. % or 0.01 to 1.5 wt. %,
fluorescing agent: 0 to 1 wt. % or 0.005 to 0.8 wt. %,
wt. % with respect to the weight of the porous dental mill blank.

According to one embodiment, the material of the porous dental zirconia mill blank is characterized as follows:
$ZrO_2$ content: 70 to 98 mol % or 80 to 97 mol %,
$HfO_2$ content: 0 to 2 mol % or 0.1 to 1.8 mol %,
$Y_2O_3$ content: 1 to 15 mol % or 1.5 to 10 mol % or 2 to 5 mol %,
$Al_2O_3$ content: 0 to 1 mol % or 0.005 to 0.5 mol % or 0.01 to 0.1 mol %.

According to a further embodiment, the material of the porous dental zirconia mill blank is characterized as follows:
$ZrO_2$ content: 90 to 98 mol %,
$HfO_2$ content: 0 to 2 mol %,
$Y_2O_3$ content: 3 to 5 mol %,
$Al_2O_3$ content: 0 to 0.1 mol %.

It was found that a higher $Y_2O_3$ content typically leads to an increase of the cubic crystal phase in the zirconia ceramic material after sintering the material to final density. A higher content of the cubic crystal phase may contribute to a better translucency.

The material of the porous dental zirconia article described in the present text may contain about 3, 4 or 5 mol % yttria. These materials are sometime referred to as 3Y-TZP, 4Y-TZP or 5-YTZP materials.

It has been found that these materials are particularly useful for producing an aesthetic zirconia restoration in a firing process as described in the present text.

In another embodiment, the material of the porous dental zirconia article comprises:
$ZrO_2+HfO_2$: 90 to 95 wt. %;
$Y_2O_3$: 4 to 10 wt. %;
$Al_2O_3$: 0 to 0.15 wt. %;
colouring oxides: 0.01 to 2 wt. %;
wt. % with respect to the weight of the porous dental zirconia article.

There is no need for alumina to be present, however, the presence of a small amount of alumina may be beneficial as it may contribute to a better hydrothermal stability of the zirconia article after sintering.

However, too high an amount of alumina may have a negative impact on the translucency of the zirconia article after sintering.

Thus, alumina may be present in an amount of 0 to 0.15 wt. %, or 0 to 0.12 wt. % or 0 to 0.1 wt. %.

The material of the porous dental zirconia article does typically not comprise the following components alone or in combination before the firing process with the surface treating agent comprising the glass is conducted: glass or glass ceramic; oxides of Si, Fe, K, Na; in an amount above 1 wt. % with respect to the weight of the material of the porous zirconia dental article.

The presence of these elements may negatively affect the overall performance of the porous dental zirconia article during machining or sintering the machined articles.

The invention also relates to the sintered dental zirconia restoration, obtainable or obtained by the process described in the present text.

The sintered dental zirconia restoration described in the present text has preferably a translucency of 25% or more or 30% or more, if determined on a 1 mm thick sample with a wave length from 450 to 800 nm in reflectance mode.

The sintered dental zirconia restoration obtained or obtainable by the process described in the present text contains different sections or zones. The sintered dental zirconia restoration comprises a glass layer section.

The glass layer section typically has a layer thickness of 5 to 200 µm or 10 to 150 µm or 20 to 100 µm.

The sintered dental zirconia restoration comprises an intermediate layer section adjacent to the glass layer section. The intermediate layer section contains a zirconia material section infiltrated by glass.

The intermediate layer section typically has a layer thickness of 0.01 to 5 µm or 0.02 to 4 µm or 0.03 to 3 µm or 0.05 to 2 µm or 0.1 to 1 µm.

The sintered dental zirconia restoration comprises a zirconia material section adjacent to the intermediate layer section.

The zirconia material section is adjacent to the intermediate layer section and does not contain glass. The thickness of the zirconia material section depends on the shape of the dental restoration. The thickness is typically within a range of 0.1 mm to 10 mm or of 0.2 to 8 mm. The shape of the sintered dental zirconia restoration is not particularly limited.

The sintered dental zirconia article may have the shape of a dental bridge, crown, abutment, or parts thereof.

If the porous dental zirconia article is sintered without a glass, the respective sintered dental zirconia article can typically be characterized by the following features alone or in combination:
a) density: at least 98.5 (in some embodiments, 99, 99.5, 99.9, or even at least 99.99) percent of theoretical density
b) biaxial flexural strength: 500 to 1,500 MPa or 800 to 1,400 MPa, determined according to ISO 6872:2015;
c) Vickers hardness: 450 MPa to 2,200 MPa, or 500 MPa to 1,800 MPa HV(2);
d) phase content tetragonal phase: 10 to 80 wt. % or 20 to 70 wt. % or 40 to 70 wt. %;
e) phase content cubic phase: 10 to 80 wt. % or 20 to 70 wt. % or 30 to 60 wt. %;
f) translucency: 25% or more, determined on a sample having a thickness of 1 mm in reflection mode at a wave length of 450 to 800 nm;
g) being tooth coloured.

A combination of the following features is sometimes preferred: a) and b); a) and c); a), d) and e); or a), b), d), e) and f).

According to one embodiment, the dental zirconia article sintered without a glass is characterized by the following features alone or in combination:
a) density: at least 98.5 percent of theoretical density
b) biaxial flexural strength: 800 to 1,400 MPa, determined according to ISO 6872:2015;
c) Vickers hardness: 500 MPa to 1,800 MPa HV(2);
d) phase content tetragonal phase: 40 to 70 wt. %;
e) phase content cubic phase: 30 to 60 wt. %;

h) translucency: 25% or more, determined on a sample having a thickness of 1 mm in reflection mode at a wavelength of 450 to 800 nm.

A combination of the following features is sometimes preferred: a) and b); a) and c); a), d) and e); or a), b), d), e) and f).

The invention also relates to a kit of parts. The kit of parts is for producing a sintered dental zirconia restoration, in particular for use in a firing process as described in the present text.

The kit of parts comprises a porous dental zirconia mill blank and a surface treating agent.

The material of the porous dental zirconia mill blank has an average connected pore diameter in the range of 40 to 150 nm. This range includes ranges of 40 nm to less than 90 nm and ranges of 90 nm to 150 nm. The surface treating agent comprises a glass.

The glass may have a viscosity of at least $10^4$ Pa*s or at least $10^5$ Pa*s at a temperature of 1,300° C.

The material of the porous dental zirconia mill blank and the surface treating agent or the glass contained therein are the same as described in the present text.

The glass contained in the surface treating agent can typically be characterized by the following features alone or in combination:

a) viscosity: at least $10^4$ Pa*s at a temperature range of 1,300° C.;

b) coefficient of thermal expansion: $1*10^{-6}K^{-1}$ to $10*10^{-6}K^{-1}$ or $2.5*10^{-6}K^{-1}$ to $9*10^{-6}K^{-1}$;

c) surface tension: of 210 to 300 mN/m at 1,300° C.;

d) Littleton softening point viscosity at a temperature of 1,100° C. to 1,350° C.;

e) flow point viscosity at a temperature of 1,300° C. to 1,650° C.;

A combination of the following features is sometimes preferred: a) and b); a) and c); a) and d); a) and e); a) and f), a), b) and c), A), b) and d); a), b) and e); a, b), d) and f).

The glass typically has a sufficiently high viscosity at the sintering temperature, so that the glass does not migrate into the pores of the porous zirconia dental article to a degree more than what is desired.

It can be beneficial, if the value of the coefficient of thermal expansion of the glass is smaller than the thermal expansion of the zirconia material. This may help to increase the compressive strength of the final dental restoration and might facilitate the provision of a durable dental restoration.

The glass can be provided in different shapes, including a powder, paste, coping, facing, or sheet form.

If the glass is provided as a powder, the Dso particle size is typically in the range of 1 to 40 μm or 2 to 30 μm. The size of the particles is typically in a range of 0.1 μm to 50 μm or 0.25 μm to 40 μm.

Ideally, the particle size of the glass powder is in a range which allows a homogenous melting of the glass powder during the sintering process of the porous zirconia dental article.

If desired, the particle size and viscosity, can be determined or obtained as described in the example section.

The glass is typically a silica-based glass. The glass typically comprises at least 80 mol % $SiO_2$.

The glass may be characterized by comprising the following composition:
$SiO_2$: 80 to 98 mol %,
$B_2O_3$: 2 to 15 mol %;
mol % with respect to the composition of the glass powder.

According to other embodiments, the glass is characterized by comprising either of the following compositions:

| | | | | | |
|---|---|---|---|---|---|
| $SiO_2$ | 80 to 98 | 80 to 98 | 80 to 98 | 80 to 98 | 80 to 98 |
| $B_2O_3$ | 0 to 15 | 0 to 15 | 2 to 15 | | |
| $Na_2O$ | 0 to 5 | 0 to 5 | | | |
| $K_2O$ | 0 to 5 | 0 to 5 | | 0.1 to 5 | 0.1 to 5 |
| $Al_2O_3$ | 0 to 5 | 0 to 5 | 0.1 to 5 | 0.1 to 5 | 0.1 to 5 |
| $La_2O_3$ | 0 to 1 | 0 to 1 | | | |
| MgO | 0 to 5 | 0 to 5 | | 0.1 to 5 | 0.1 to 5 |
| CaO | 0 to 2 | 0 to 2 | | | |
| SrO | 0 to 2 | 0 to 2 | | | |
| BaO | 0 to 2 | 0 to 2 | | | |
| $Bi_2O_3$ | 0 to 0.5 | 0 to 0.5 | | | |

The amounts are given in mol % with respect to the glass composition.

The glass typically does not comprise the following components alone or in combination:
$Li_2O$ in an amount of more than 0.1 mol %;
F in an amount of more than 0.1 mol %;
$P_2O_5$ in an amount of more than 0.1 mol %.

The presence of these components may negatively affect properties like melting behaviour, surface tension, or viscosity of the glass.

The surface treating agent may further comprise a liquid for dispersing the glass, if provided as powder.

Thus, the surface treating agent may be a powder, a dispersion or a paste.

The dispersion of the glass powder in a liquid typically facilitates the application of the glass powder to the surface of the porous dental zirconia article.

The nature of the liquid is not particularly limited, unless the desired effect cannot be achieved.

The liquid should have a boiling point allowing the liquid to evaporate during the fast firing process without complications, or during a drying step which is optionally carried out before the firing process is started.

The liquid should not contain components or chemical elements which may cause damage to the sintering furnace used for the fast firing process.

Using liquids which do not contain halogen components (e.g. F, Cl, Br) is sometimes preferred.

The boiling point of the liquid should not be too high. Otherwise the evaporation of the liquid during the firing process might not be sufficiently fast.

The boiling point of the liquid may also be adjusted by using liquids having a suitable molecular weight.

It is beneficial, if the viscosity of the liquid is such that the glass powder can be easily dispersed.

The liquid can typically be characterized by the following features alone or in combination:
molecular weight (Mw): 18 to 1,000 g/mol;
boiling point: 50 to 300° C.;
viscosity: 1 to 2,000 mPa*s or 10 to 1,500 mPa*s or 100 to 1,000 mPa*s (measured at 23° C. at a shear rate of 50 s$^{-1}$).

Mw (substance) is the average molecular weight, if a polymer is used.

Suitable liquids include water and alcohol (including polyalcohols, such as polyethylene glycol) and mixtures thereof.

According to one embodiment, the solvent is water.

According to another embodiment, the solvent is different from water.

The liquid or solvent is typically miscible with water.

Useful liquids include polyol(s) (including polyvinyl alcohol), glycol ether(s) (e.g., PEG 200, PEG 400, PEG 600, diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof.

If a liquid is present, the glass powder to liquid ratio in the glazing composition is typically in a range of 1:1 to 1:15 or 1:2 to 1:12 by weight.

The surface treatment agent may also contain a colourant.

Adding a colourant can be beneficial to enhance the visibility of the surface treating agent during use, especially, if the surface treating agent is transparent or of the same colour as the zirconia milled restorations.

Thus, the practitioner can easily determine to which parts of the surface of the dental article the surface treating agent has already been applied and which parts have not been treated yet and should remain untreated. The colourants, which are typically of organic nature will be burnt out during a later sintering step and thus not be incorporated into the dental article.

Examples of soluble colourants which can be used include Riboflavin (E101), Ponceau 4R (E124), Green S (E142).

The surface treating agent is typically contained in a receptacle, e.g. a vessel, bottle, or flask.

Thus, the kit of parts of the present text comprises as separate parts: porous dental zirconia mill blank, surface treating agent containing a glass, and optionally liquid for dispersing the glass if provided as powder.

The kit of parts is typically provided to the practitioner with an instruction of use.

The instruction of use contains information for what purpose the kit of parts is intended to be used, how the machining should be done and what sintering conditions should be applied.

If desired, the kit of parts may further comprise one or more of the following items:
  sintering aids,
  application device for the surface treating agent,
  optionally a shade guide,
  optionally polishing aids,
  optionally a sintering oven.

Sintering aids include e.g. sintering beads and other equipment suitable for mechanically supporting the article to be sintered during the sintering process.

Application devices include e.g. brushes, brush pens, sponges, and spray devices.

As the fast firing process described in the present text is typically done in a short period of time, a sintering oven or furnace should be used which has the capability to provide heating rates up to 7K/sec.

The invention also relates to the use of the surface treating agent and/or the dental zirconia article described the present text for producing a dental zirconia restoration in fast firing process as described in the present text.

The invention further relates to the use of the kit of parts described in the present text for the production of a dental restoration, preferably by applying the process described in the present text.

Further embodiments of the invention are outlined below:

Embodiment 1

A kit of parts for use in a process as described in the present text or for producing a sintered dental article described as described in the present text, the kit of parts comprising a porous dental zirconia mill blank and a surface treating agent,
  the material of the porous dental zirconia mill blank being characterized as follows:
    being composed of zirconia with an yttria content of about 3 or 4 or 5 mol %,
    having an average connected pore diameter of 40 to 150 nm, and
    having a porosity of 30 to 70%,
  the surface treating agent being characterized as follows:
    comprising a glass powder,
      the glass powder having a $D_{50}$ particle size in the range of 1 to 40 µm, and
      the glass of the glass powder having a viscosity of at least $10^4$ Pa*s at a temperature of 1,300° C.

Embodiment 2

A process of producing a dental zirconia article,
  the dental zirconia article having an outer and an inner surface,
  the process comprising the step of
    firing a porous dental zirconia article and a glass powder to obtain a sintered dental zirconia article,
    the glass powder being located during the firing step on at least a portion of the outer surface of the porous dental zirconia article,
  wherein the porous dental zirconia article has an average connected pore diameter in the range of 40 to 150 nm,
  wherein the glass has a viscosity of at least $10^4$ Pa*s at a temperature of 1,300° C., and
  wherein during the firing step the glass infiltrates the pores of the porous dental zirconia article to an extent of not more than 5 µm in depth.

Embodiment 3

A process of producing a dental zirconia article,
  the dental zirconia article having an outer and an inner surface,
  the process comprising the step of
    firing a porous dental zirconia article and a glass powder to obtain a sintered dental zirconia article,
    the glass powder being located during the firing step on at least a portion of the outer surface of the porous dental zirconia article,
  wherein the porous dental zirconia article has an average connected pore diameter in the range of 40 to 150 nm,
  wherein the glass has a viscosity of at least $10^5$ Pa*s at a temperature of 1,300° C., and
    wherein during the firing step the glass infiltrates the pores of the porous dental zirconia article to an extent of not more than 5 µm in depth.

Embodiment 4

A process of producing a dental zirconia article,
  the dental zirconia article having an outer and an inner surface,
  the process comprising the step of
    firing a porous dental zirconia article and a glass powder to obtain a sintered dental zirconia article,
    the glass powder being located during the firing step on at least a portion of the outer surface of the porous dental zirconia article,
  wherein the porous dental zirconia article has an average connected pore diameter in the range of 40 to 150 nm,
    wherein the glass has a viscosity of at least $10^5$ Pa*s at a temperature of 1,300° C., and
  wherein during the firing step the glass infiltrates the pores of the porous dental zirconia article to an extent of not more than 5 µm in depth wherein the glass is characterized by comprising either of the following compositions:

| | | | | | |
|---|---|---|---|---|---|
| SiO$_2$ | 80 to 98 | 80 to 98 | 80 to 98 | 80 to 98 | 80 to 98 |
| B$_2$O$_3$ | 0 to 15 | 0 to 15 | 2 to 15 | | |
| Na$_2$O | 0 to 5 | 0 to 5 | | | |
| K$_2$O | 0 to 5 | 0 to 5 | | 0.1 to 5 | 0.1 to 5 |
| Al$_2$O$_3$ | 0 to 5 | 0 to 5 | 0.1 to 5 | 0.1 to 5 | 0.1 to 5 |
| La$_2$O$_3$ | 0 to 1 | 0 to 1 | | | |
| MgO | 0 to 5 | 0 to 5 | | 0.1 to 5 | 0.1 to 5 |
| CaO | 0 to 2 | 0 to 2 | | | |
| SrO | 0 to 2 | 0 to 2 | | | |
| BaO | 0 to 2 | 0 to 2 | | | |
| Bi$_2$O$_3$ | 0 to 0.5 | 0 to 0.5 | | | | wherein the amounts are given in mol % with respect to the glass composition.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Methods
Ion Concentration If desired, the concentration of ions can be determined by X-ray fluorescence spectrometry (XRF). Some XRF devices offer the possibility to directly measure ion concentrations in liquid solutions, e.g. the ZSX Primus II from Rigaku, Japan.
Fluorescence If desired, the samples are placed in an UV-light box used for inspection of e.g. thin layer chromatography plates. Fluorescence can be detected by the human eye as by the lighting up of the sample against a black background.
BET Surface The BET surface of a porous article is typically determined as follows: Total pore volume and average pore diameter can be analyzed with the use of N$_2$ sorption isotherms and BET surface area analysis. Samples of around 0.1-2 grams were cut if necessary from larger samples in order to be inserted in to the straight tubes. All samples are degassed in vacuum for more than 1 h at 120° C. before analysis. The samples are then analyzed by adsorption and desorption of N$_2$ gas with a Belsorb II (distributed by Robotherm Prazisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (Details see Chapter 12 regarding calculation see Belsorb Analysis Software User Manual Operating Manual, Chapter 12, Bel Japan. INC).
Method for Measuring Translucency (TL)

If desired, the translucency of the ceramic articles can be evaluated with the following procedure: A test piece in the shape of a disc with an approximate thickness of 1±0.05 mm and an area of measurement of at least 12 mm in diameter is provided. For preparation of the test pieces the pre-sintered sample is sawn into wafers with a thickness of approximately 1.3 mm using a dry cut saw. The parallel large faces of the wafer are ground using silicon carbide sand paper (P2500). The ground samples are sintered in an appropriate furnace to a sintered sample with a thickness of 1±0.05 mm. The sintered sample is measured as fired with a spectrophotometer (X-Rite Color i7, Grand Rapids, USA) in reflectance mode against a white and a black background to obtain the opacity of the material. Translucency is calculated according to T=1−opacity. Higher values of translucency are indicative of greater transmission of light, and less opacity.

If desired, L*a*b* values can be determined in addition to opacity using the same equipment.
Particle Size (Suitable for Micro-Sized Particles)

If desired, the particle size distribution including the mean particle size can be determined with a Cilas 1064 (FA. Quantacrome) particle size detection device.
Density If desired, the density of the sintered material can be measured by an Archimedes technique. The measurement is made on a precision balance (identified as "BP221S" from Sartorius AG, Göttingen, Germany) using a density determination kit (identified as "YDK01" from Sartorius AG). In this procedure, the sample is first weighed in air (A), then immersed in water (B). The water is a 0.05 wt. % tenside solution (e.g. "Berol 266, Fa. Hoesch). The density is calculated using the formula $\rho=(A/(A-B))\,\rho 0$, where $\rho 0$ is the density of water. The relative density can be calculated by reference to the theoretical density ($\rho t$) of the material, $\rho_{rel}=(\rho/\rho t)100$.
Porosity If desired, the porosity can be determined as follows: Porosity=(1−(density of porous material/density of sintered material))×100. The density of the porous material can be calculated by the division of weight and volume. Volume can be obtained by geometrical measurements.
Average Connected Pore Diameter If desired, the average connected pore diameter can be determined as follows: Mercury is introduced in the porous material under high pressure using a porosimeter (Quantachrome Poremaster). The applied pressure is related to pore size by the opposing force of the surface tension of Mercury. Using the so-called Washburn equation, the average connected pore diameter can be determined. The following measurement parameters are applied or used for result calculation: Pressure range from 20 to 60000 PSIA, temperature during measurement 20° C., Hg Contact Angle 140° and Hg Surface Tension 480 mN/m.
Average Grain Size If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts.

The average distance for each line is multiplied by 1.56 to determine the grain size and this value is averaged over all the lines for all micrographs of each sample.

Biaxial Flexural Strength

If desired, the biaxial flexural strength of pre-sintered material can be determined according to ISO 6872:2015 with the following modifications: The pre-sintered sample is sawn into wafers with a thickness of 2+/−0.1 mm using a dry cut saw. The diameter of the samples should be 17+/−2 mm. The parallel large faces of the wafer are ground using silicon carbide sand paper (P2500). Each wafer is centred on a support of three steel balls (diameter of the balls 6 mm) with a support diameter of 14 mm. The punch diameter in contact with the wafer is 3.6 mm. The punch is pushed onto the wafer at a rate of 0.1 mm per min. A minimum of 15 samples is measured to determine the average strength. The tests can be conducted in an Instron 5566 universal testing machine (Instron Deutschland GmbH).

Vickers Hardness

If desired, the Vickers hardness can be determined according to ISO 843-4 with the following modifications: The surface of the pre-sintered samples is ground using silicon carbide sand paper (P2500). The surface of the sintered samples is polished with 20 μm diamond suspension. The test forces are adjusted to the hardness level of samples. Used test forces are between 0.2 kg and 2 kg and are applied for 15 s each indentation. A minimum of 10 indentations is measured to determine the average Vickers hardness. The tests can be conducted with a hardness tester Leco M-400-G (Leco Instrumente GmbH).

Thickness of Infiltration Zone

If desired, the thickness of the infiltration zone can be determined by scanning electron spectroscopy (SEM). A manually sanded (sandpaper P2500) zirconia disc sample (2 mm thick) is treated with a glazing composition, fired according to the respective sintering protocol and analyzed with a scanning electron microscope Leco M-400-G2.

This technology can also be used for visualizing the closing of the pores during the sintering process.

Viscosity of Glass/Surface Tension

If desired, the viscosity and surface tension of the glass can be calculated using the software tool from SciGlass. In more detail, for calculating the properties of glass compositions described in the present text, the following software tool was used: SciGlass Professional, Version 7.12, Model Priven 2000.

Materials

The following materials were used:

|  | Description |
| --- | --- |
| 3Y-TZP (Lava ™ Plus) | Porous dental zirconia article |
| Glass G1 | Experimental glass powder (surface treating agent) |
| Glass G2 | Experimental glass powder (surface treating agent) |
| Glass G3 | Glass powder (surface treating agent); composition according to specification provided by supplier |
| Iso-propanol | Liquid (part of the surface treating agent) |

Process for Producing Mill Blanks

General Description

Mill blank samples were produced from a 3Y-TZP powder. The following steps were applied:

Filling the powder composition in a mould (diameter: 24.9 mm).

Applying pressure (200 MPa) to the powder filling.

Demoulding the compacted body.

Applying a heat treatment at 970° C. for about 2 hours.

The material of the mill blanks had an average connected pore diameter of about 78 nm.

Process for Producing Test Samples

Samples were cut from the mill blank samples (sample dimensions: 1.6 mm×18.5 mm (height)×25.6 mm).

Process for Producing Glass Powder

Glass powders G1 and G2 were produced as follows:

The respective oxides were weighed and filled into a poly propylene bottle. Isopropyl Alcohol was added until a slurry was obtained. Zirconia milling media was added, and the mixtures were rolled on a roller mill over-night. The mixture was screened into a plastic petry dish and dried. The dried powder was filled into an alumina crucible and calcined at 800° C. for 2 hrs. The calcined powder was filled into a Pt/Rh crucible, heated to 1,550° C., and held at 1,550° C. for 2 hrs. The molten glass was cooled down by quenching in de-ionized water. The glass was crushed and ball milled to obtain a milled glass powder with a mean particle size of 2.5 μm.

The Glass Powders used had the following composition and properties:

|  | G1 | G2 | G3 |
| --- | --- | --- | --- |
| $SiO_2$ | 93 mol % | 90 mol % | 50-92 mol % |
| $B_2O_3$ | 5 mol % | 10 mol % | 0-10 mol % |
| $Al_2O_3$ | 2 mol % |  | 3.5-20 mol % |
| CaO |  |  | 0-5 mol % |
| $Na_2O$ |  |  | 3-18 mol % |
| $K_2O$ |  |  | 1.5-12 mol % |
| ZnO |  |  | 0-3 mol % |
| SrO |  |  | 0.004-5 mol % |
| $Li_2O$ |  |  | 0-9 mol % |
| $La_2O_3$ |  |  | 0.005-1 mol % |
| $CeO_2$ |  |  | 0-1 mol % |
| $SnO_2$ |  |  | 0.001-1 mol % |
| $P_2O_5$ |  |  | 0-3 mol % |
| F |  |  | 0-5 mol % |
| Viscosity at 1,300° C.** | 6.3 | 6.3 | 3.7 |
| Viscosity at sintering temperature** | 3.9 | 5.5 | 2.1 |

**Calculated and given in $\log_{10}$ (Pa*s)

Process for Surface-Treatment 1 g of the Glass Powder was dispersed in 2 ml of iso-propanol to obtain a dispersion of the Glass Powder in a liquid. The dispersion was applied to one side of the test samples using a fixative spray nozzle attached to a can of Dust-off™.

Firing Process

The surface-treated test samples were heat-treated according to the following Sinter Protocol using a CEREC Speed-Fire™ furnace from Dentsply Sirona.

Sinter Protocol a) a first heat-treating segment up to a temperature of about 1,350° C., which is reached within about 4 min (heating rate 5.3 K/s), b) a second heat-treating segment up to a temperature of about 1,580° C., which is reached within about 9.5 min (heating rate 0.4 K/s) and c) a third heat-treating segment (dwell time) for about 2 min and d) a cooling-down segment to 1,000° C., which is reached within about 3 min.

After cooling, the samples were investigated with respect to infiltration depth and translucency.

Results:

|  | Ex1 | Ex2 | Comp. Ex1 |
|---|---|---|---|
| Test Sample treated with | G1 | G2 | G3 |
| Infiltration Depth of Glass [µm] | Low; below 5 µm | Low; below 5 µm | High; above 5 µm |
| Translucency [%] | High | High | Low |

Findings:

If the process and materials according to the invention were used, the infiltration depth of the glass into the pores of the porous zirconia article was low and the obtained sintered zirconia article showed a high translucency.

Figure 2:
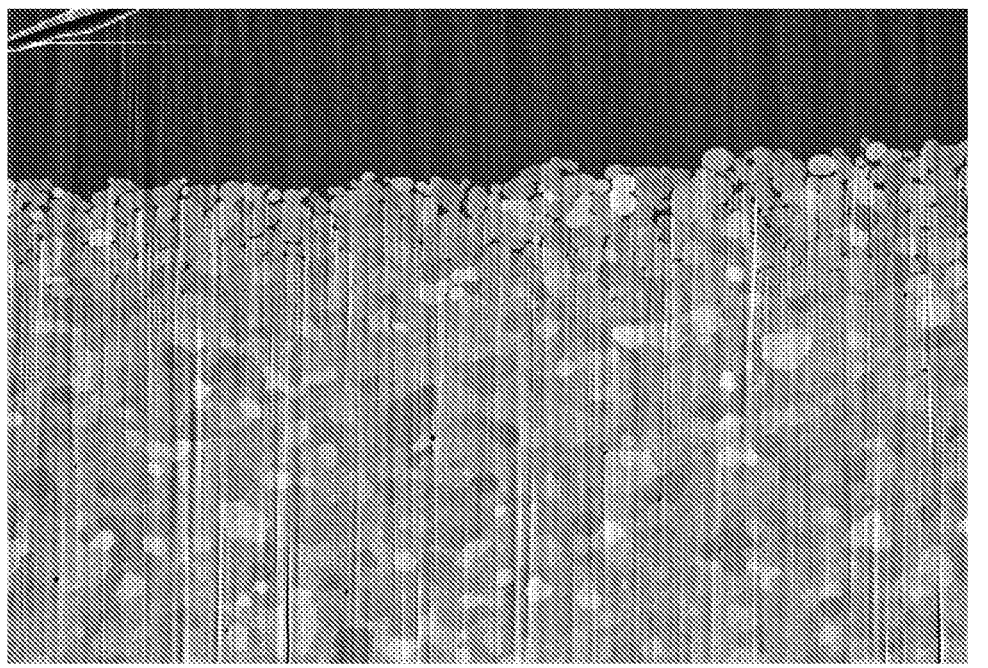
FIG. 2 shows a SEM picture of a zirconia sample according to the invention where the glass has only infiltrated the pores of the porous zirconia material up to a depth of less than 5 μm.
Figure 3:
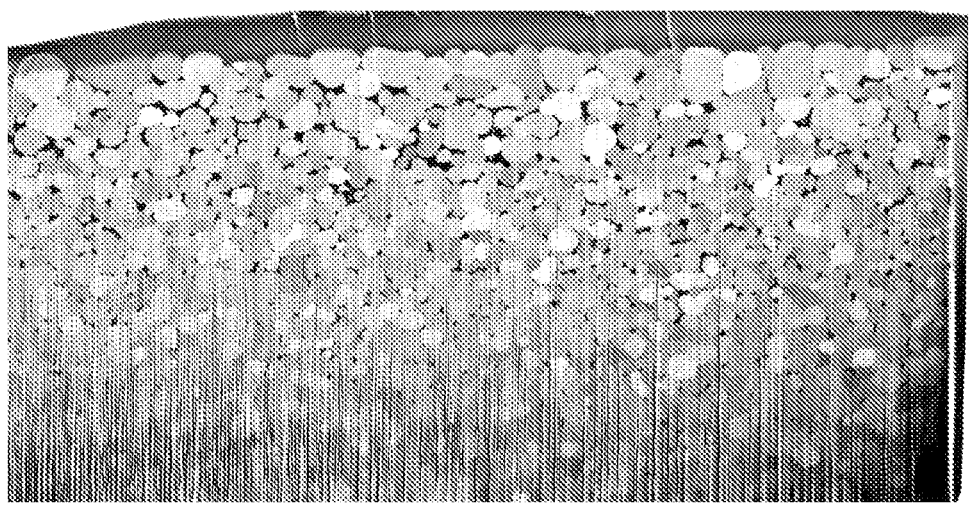
FIG. 3 shows a SEM picture of a zirconia sample where the glass has impregnated a substantial part of the porous zirconia material.

SEM pictures for the samples of Ex1 and Comp. Ex1 are shown in FIG. 2 and FIG. 3.

For Ex1 an interpenetration depth of the glazing of 1-2 µm was observed.

For Comp. Ex1 an interpenetration depth of the glazing of 7-8 µm was observed.

What is claimed is:

1. A process for producing a sintered dental zirconia restoration, the process comprising:
   providing a porous dental zirconia restoration,
      the porous dental zirconia restoration comprising a surface-treating agent disposed on an outer surface of the porous dental zirconia restoration,
      the porous dental zirconia restoration comprising pores having an average connected pore diameter from 40 to 150 nm, and
      the surface-treating agent comprising a glass, the glass characterized by a viscosity of at least $10^4$ Pa*s at a temperature of 1,300° C.; and
   firing the porous dental zirconia restoration,
   wherein the firing is effective to allow the glass to infiltrates the pores of the porous dental zirconia restoration not more than 5 µm in depth.

2. The process according to claim 1, the glass having a viscosity of at least $10^5$ Pa*s at the temperature of 1,300° C.

3. The process according to claim 1, the glass and the zirconia material of the porous dental zirconia restoration being characterized as follows:
   the glass being characterized by a viscosity at least $10^5$ Pa*s at a temperature of 1,300° C., and
   the pores having an average connected pore diameter in the range of 90 to 150 nm.

4. The process according to claim 1,
   the firing comprising:
   a first heat-treating segment,
      the first heat-treating segment being conducted with a heating rate of at least 3 K/sec, until a temperature level of 75 to 90% of a final sintering temperature of the dental zirconia restoration is achieved.

5. The process according to claim 4, the firing further comprising a second heat-treating segment following the first heat-treating segment back-to-back,
   the second heat-treating segment being conducted at a heating rate that is lower than the heating rate of the first heat-treating segment,
   the second heat-treating segment being applied until a sintering temperature of at least 1,500° C. is reached.

6. The process according to claim 5, the firing further comprising a third heat-treating segment following the second heat-treating segment back-to-back, the third heat-treating segment characterized by a dwell time of utmost 8 min.

7. The process according to claim 6, further comprising a cool-down segment following the third heat-treating segment back-to-back, the cool-down segment being characterized by the following features alone or in combination;
   cool-down rate: 3 K/sec or more;
   duration: 6 min or less.

8. The process according to claim 7, the duration of the firing and the cool-down segment being 30 min or less.

9. A sintered dental zirconia restoration prepared by the process of claim 1, characterized by a translucency of 25% or more, if determined on a 1 mm thick sample with a wave length of 450 to 800 nm in reflectance mode.

10. The sintered dental zirconia restoration of claim 9, having the following sections:
    a glass layer section,
       the glass layer section having a layer thickness of 10 to 200 µm,
    an intermediate layer section adjacent to the glass layer section,
       the intermediate layer section containing a zirconia material section infiltrated by the glass of the glass layer section,
       the intermediate layer section having a layer thickness of 0.01 to 5 µm,
    a zirconia material section adjacent to the intermediate layer section,
       the zirconia material section not containing glass.

11. A kit of parts for use in a process according to claim 1, the kit of parts comprising;
    a porous dental zirconia mill blank or the porous zirconia dental restoration having an average connected pore diameter of 40 to 150 nm, and
    a surface treating agent comprising a glass, the glass having a viscosity of at least $10^4$ Pa*s at a temperature of 1,300° C.

12. The kit of parts according to claim 11, the porous zirconia dental mill blank or the porous zirconia dental restoration comprised of a material characterized by the following features alone or in combination:
    BET surface: 5 to 15 m$^2$/g;
    density: 2 to 4 g/cm$^3$;
    porosity: 30 to 70%;
    average grain size: 50 to 200 nm;
    coefficient of thermal expansion: 8.5* $10^{-6}$K$^{-1}$ to 11.5* $10^{-6}$K$^{-1}$.

13. The kit of parts according to claim 11, the glass being characterized by the following features alone or in combination:
    being a silica-based glass;
    coefficient of thermal expansion: 1* $10^{-6}$K$^{-1}$ to 10* $10^{-6}$K$^{-1}$;
    surface tension: of 210 to 300 mN/m at 1,300° C.,
    Littleton softening point viscosity at a temperature of 1,100° C. to 1,350° C.;
    flow point viscosity at a temperature of 1,300° C. to 1,650° C.

14. The kit of parts according to claim 11, further comprising one or more of the following items:
    instruction for use;
    application device for the surface treating agent;
    sintering aids;
    liquid for dispersing the glass, if provided as powder;
    optionally a shade guide;
    optionally polishing aids;
    optionally a sintering oven.

15. The kit of parts of claim 11, the glass comprising either of the following compositions:

| | | | | | |
|---|---|---|---|---|---|
| SiO$_2$ | 80 to 98 | 80 to 98 | 80 to 98 | 80 to 98 | 80 to 98 |
| B$_2$O$_3$ | 0 to 15 | 0 to 15 | 2 to 15 | | |
| Na$_2$O | 0 to 5 | 0 to 5 | | | |
| K$_2$O | 0 to 5 | 0 to 5 | | 0.1 to 5 | 0.1 to 5 |
| Al$_2$O$_3$ | 0 to 5 | 0 to 5 | 0.1 to 5 | 0.1 to 5 | 0.1 to 5 |
| La$_2$O$_3$ | 0 to 1 | 0 to 1 | | | |
| MgO | 0 to 5 | 0 to 5 | | 0.1 to 5 | 0.1 to 5 |
| CaO | 0 to 2 | 0 to 2 | | | |
| SrO | 0 to 2 | 0 to 2 | | | |
| BaO | 0 to 2 | 0 to 2 | | | |
| Bi$_2$O$_3$ | 0 to 0.5 | 0 to 0.5 | | | | wherein the amounts are mol %.

16. The kit of parts of claim 11, the glass comprising:
SiO$_2$ present in an amount of 80-90 mol %, and
B$_2$O$_3$ present in an amount of 2-15 mol %.

17. The kit of parts of claim 11, the surface treating agent further comprising a liquid selected from water, an alcohol, a polyol, and a combination thereof.

18. The kit of parts of claim 11, the porous dental zirconia mill blank or the porous dental zirconia restoration having an average connected pore diameter in the range of 90 to 150 nm.

* * * * *